(12) United States Patent
Dijkstra

(10) Patent No.: US 9,624,507 B2
(45) Date of Patent: Apr. 18, 2017

(54) SPINACH PLANTS THAT ARE RESISTANT TO DOWNY MILDEW

(71) Applicant: NUNHEMS B.V., Nunhem (NL)

(72) Inventor: Jan Ane Dijkstra, Beegden (NL)

(73) Assignee: Nunhems B.V., Nunhem (NL)

( * ) Notice: Subject to any disclaimer, the term of this patent is extended or adjusted under 35 U.S.C. 154(b) by 208 days.

(21) Appl. No.: 14/484,324

(22) Filed: Sep. 12, 2014

(65) Prior Publication Data

US 2015/0082483 A1  Mar. 19, 2015

(30) Foreign Application Priority Data

Sep. 13, 2013 (EP) .................................... 13184388

(51) Int. Cl.
*A01H 5/12* (2006.01)
*C12N 15/82* (2006.01)
*A01H 1/04* (2006.01)

(52) U.S. Cl.
CPC ........... *C12N 15/8282* (2013.01); *A01H 1/04* (2013.01); *A01H 5/12* (2013.01)

(58) Field of Classification Search
None
See application file for complete search history.

(56) References Cited

U.S. PATENT DOCUMENTS

| | | | | |
|---|---|---|---|---|
| 7,935,866 B2 * | 5/2011 | Baerends | ................ | A01H 5/12 435/412 |
| 2012/0222147 A1 | 8/2012 | Dijkstra | | |
| 2014/0065287 A1 * | 3/2014 | den Braber | ............. | A01H 5/12 426/615 |

FOREIGN PATENT DOCUMENTS

WO  2013064436 A1  5/2013

OTHER PUBLICATIONS

Correll et al., Eur J Plant Pathol 129:193-205 (2011).*
Irish et al., Plant Dis 91:1392-96 (2007).*
Kik, Spinach Conference, Amsterdam, p. 26 (2011).*
Corell et al., Spinach: Better Management of Downy Mildew and White Rust Through Genomics, Eur J Plant Pathol (2011), vol. 129, pp. 193-205.
Smith and Zahara, New Spinach Immune to Mildew, California Agriculture (1956).
Smith et al., Downy Mildew on Spinach, California Agriculture (1961).
Smith et al., Immunity to Race 2 of Spinach Downy Mildew, Phytopathology (1962).
Brandenberger et al., Evaluation of Spinach Germplasm for Resistance to a New Race (Race 4) of *Peronospora farinosa* f. sp. spinaciae, Hort Science (1992), vol. 27, No. 20, pp. 1118-1119.
The International Seed Federation, Differential Hosts (2013); http://www.worldseed.org/isf/differential_hosts.html.
Nguyen et al., Effect of Plant Growth Regulator Combination and Culture Period on in vitro Regeneration of Spinach (*Spinacia oleracea* L.), Plant Biotechnology Reports (2013), vol. 7, No. 1, p. 99-108.
Irish et al., Three New Races of the Spinach Downy Mildew Pathogen Identified by a Modified Set of Spinach Differentials, Plant Disease (2007), vol. 91, No. 11, pp. 1392-1396.
Corell et al., Guidelines for Spinach Downy Mildew: *Peronospora farinosa* f. sp. spinaciae (Pfs), found on the website of the ISF (International Seed Federation) (2010).
Ranganathan, Differential Sets—*Peronospora farinosa* f. sp. spinaciae (PFS)—Spinach (2013), http://www.worldseed.org/cms/medias/file/TradeIssues/DiseasesResistance/Differentials/Spinach-downy_mildew_2013.pdf.
Extended European Search Report issued in corresponding Application No. EP13184388.0, dated Jan. 2, 2014.

* cited by examiner

*Primary Examiner* — Amjad Abraham
*Assistant Examiner* — Russell Boggs
(74) *Attorney, Agent, or Firm* — Arent Fox LLP

(57) ABSTRACT

The present invention relates to the field of spinach breeding, in particular to a new dominant resistance gene, designated RPF11, which confers resistance against races 7 to 14 of *Peronospora farinosa* and to spinach plants comprising said gene.

21 Claims, No Drawings

SPINACH PLANTS THAT ARE RESISTANT TO DOWNY MILDEW

CROSS-REFERENCE TO RELATED APPLICATIONS

This application claims the benefit of European Application No. 13184388.0, filed Sep. 13, 2013, the contents of which are hereby incorporated by reference in its entirety.

FIELD OF THE INVENTION

The invention relates to a new dominant resistance gene, designated RPF11, for use in breeding downy mildew resistant spinach plants. The present invention further relates to cultivated spinach (*Spinacia oleracea*) seeds, plants and plant parts (e.g. leaves) grown from the seeds, that are resistant to *Peronospora farinosa* f. sp. *spinaciae* (abbreviated herein as Pfs) due to the presence of RPF11 in their genome, as well as to progenies of the plants and propagation material for producing the plants.

BACKGROUND OF THE INVENTION

Spinach (*Spinacia oleracea*) has become an important vegetable crop in many parts of the world, with the top spinach producing county being China (>80% of global production), followed by USA, Japan and various European countries. Globally about 1 million ha of spinach are grown in Asia and about 35,000 ha in each of the EU, USA and Japan (see Correll et al. (2011, Eur J Plant Pathol 129: 193-205). Part of the increase in spinach demand is likely due to an increased health-consciousness of consumers and the beneficial properties of spinach. Spinach leaves are rich in beta-carotene, lutein, folic acid, vitamin C, calcium, iron and antioxidants. Especially the demand for fresh spinach has significantly increased over the last years.

Due to this increase in production over the last 10-15 years, incidence and severity of one of the most damaging pathogens of spinach, downy mildew of spinach, caused by races of the oomycete *Peronospora farinosa* f. sp. *spinaciae* (Pfs; synonym *P. effusa*) has increased concomitantly. Before 1990 only three races of Pfs were known, however between 1990 and 2010 ten new races were identified. The emergence of new races of Pfs makes this pathogen a major threat for spinach production globally and identifying new sources of resistance is therefore necessary.

Historically, Pfs race 1 (Pfs:01 or Pfs1) was first reported in 1824 and resistance to race 1 was identified later in two Iranian accessions (PI140467 and PI140464) and incorporated into commercial hybrid varieties, such as Califlay (Smith and Zahara, California Agriculture, July 1956). In 1958 race 2 appeared and a few years later a single dominant gene imparting resistance against both race 1 and race 2 was identified (Smith et al. 1961 and 1962). In 1976 race 3 appeared and again several years later resistance against race 3 was found. Race 4 was only identified in 1990, and Brandenberger et al. (1992) identified accessions CGN09546, of which 60% of individual plants were resistant, and SP1 82/87, of which 80% of individual plants were resistant. The rapid emergence of new races hereafter, lead to the identification of new resistance genes and their incorporation into commercial varieties, as indicated in Table 1 below (− means resistant reaction; + means susceptible reaction; (−) means reduced level of infection often referred to as field resistance, i.e. sparse sporulation on the tips of the cotyledons; +/−means undecided). These varieties are also used as host differentials for determining the race of isolates of Pfs (see document of the International Seed Federation, August 2013; World Wide Web Worldseed.org.

TABLE 1

| Variety | Pfs1 | Pfs2 | Pfs3 | Pfs4 | Pfs5 | Pfs6 | Pfs7 | Pfs8 | Pfs9 | Pfs10 | Pfs11 | Pfs12 | Pfs13 | Pfs14 |
|---|---|---|---|---|---|---|---|---|---|---|---|---|---|---|
| Viroflay | + | + | + | + | + | + | + | + | + | + | + | + | + | + |
| Resistoflay | − | − | + | + | + | + | + | + | + | + | + | + | + | + |
| Califlay | − | + | − | + | − | + | + | − | − | + | − | − | + | − |
| Clermont | − | − | − | − | + | + | + | + | + | + | + | + | + | + |
| Campania | − | − | − | − | − | + | − | + | + | + | − | + | +/− | + |
| Boeing (=Avenger in USA) | − | − | − | − | − | − | − | + | − | + | − | + | − | + |
| Lion | − | − | − | − | − | − | − | − | − | + | − | − | − | − |
| Lazio | − | − | − | − | − | − | − | − | − | − | + | + | + | + |
| Whale | − | − | − | (−) | − | (−) | (−) | − | − | + | − | − | + | (−) |

Commercial spinach varieties are mostly hybrids, produced by crossing a male and a female inbred line, although also some open pollinated varieties exist. The male and female parent line generally each carry a different resistance gene. For example, the hybrid variety *Andromeda* (Nunhems; see patent application US2012/0222147) is resistant against Pfs 1-12 and Pfs14. Resistance against Pfs 1, 3, 5, 8, 9, 11, 12 and 14 is conferred by a resistance gene from one parent, while resistance against Pfs 1-10 is conferred by a resistance gene from the other parent.

WO2013/064436 describes a dominant resistance gene, called R6, which confers resistance against Pfs1-6, 9, 11-14 (see Table 1 on page 19 of WO2013/064436; in 2011 the type strain UA4410 has been designated Pfs14 by the International Working Group on *Peronospora farinosa*, IWGP).

To achieve resistance against all known Pfs races (Pfs1-14) using the known resistance genes, one would for example need to combine the resistance genes of Lazio and Lion. To date no single resistance gene is known, which confers resistance against all known Pfs races, or especially against Pfs races 7-14.

SUMMARY OF VARIOUS EMBODIMENTS OF THE INVENTION

It is, therefore, an object of the invention to provide a single dominant resistance gene, which confers resistance against at least Pfs races 7-14. In addition, the gene optionally also confers resistance against one or more (or all) of Pfs races 1-6. Optionally the gene also confers resistance against isolate UA4712. Thus, in one aspect, the resistance gene, designated RPF11, confers resistance against at least Pfs races 7-14, and optionally also against isolate UA4712 and/or optionally against one or more of Pfs 1-6. In a further aspect, seeds, plants and plant parts or cultivated spinach comprising the new major resistance gene are provided.

Also methods for identifying and/or selecting spinach plants comprising the resistance gene are provided, as are methods for transferring the resistance gene from seeds deposited under accession number NCIMB 42158 into different spinach plant lines or varieties.

DEFINITIONS

The indefinite article "a" or "an" does not exclude the possibility that more than one of the element is present, unless the context clearly requires that there be one and only one of the elements. The indefinite article "a" or "an" thus usually means "at least one".

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"Spinach" or "cultivated spinach" or "cultivated *Spinacia oleracea*" refers herein to plants of the species *Spinacia oleracea* (or seeds from which the plants can be grown), and parts of such plants, bred by humans for food and having good agronomic characteristics. This includes any cultivated spinach, such as breeding lines (e.g. backcross lines, inbred lines), cultivars and varieties (open pollinated or hybrids). This includes any type of spinach, such as savoy, flat- or smooth-leaf spinach or semi-savoy types. Wild spinach (i.e. not cultivated spinach) or wild relatives of spinach, such as *Spinacia tetrandra* and *Spinazia turkestanica*, are not encompassed by this definition.

As used herein, the term "plant" includes the seed (from which the plant can be grown), the whole plant or any parts such as plant organs (e.g., harvested or non-harvested leaves, etc.), plant cells, plant protoplasts, plant cell- or tissue cultures from which whole plants can be regenerated, propagating or non-propagating plant cells, plants cells which are not in tissue culture (but which are for example in vivo in a plant or plant part), plant callus, plant cell clumps, plant transplants, seedlings, plant cells that are intact in plants, plant clones or micro-propagations, or parts of plants (e.g., harvested tissues or organs), such as plant cuttings, vegetative propagations, embryos, pollen, ovules, flowers, leaves, heads, seeds (produced on the plant after self-fertilization or cross-fertilization), clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves. When "seeds of a plant" are referred to, these either refer to seeds from which the plant can be grown or to seeds produced on the plant, after self-fertilization or cross-fertilization.

"Somatic cells" and "reproductive cells" can be distinguished, whereby somatic cells are cells other than gametes (e.g. ovules and pollen), germ cells and gametocytes. Gametes, germ cells and gametocytes are "reproductive cells".

"Tissue Culture" or "cell culture" refers to an in vitro composition comprising isolated cells of the same or a different type or a collection of such cells organized into plant tissue. Tissue cultures and cell cultures of spinach, and regeneration of spinach plants therefrom, is well known and widely published (see, e.g. Nguyen et al., 2013, Plant Biotechnology Reports, Vol. 7 Issue 1, p 99).

"Harvested plant material" refers herein to plant parts (e.g., leaves detached from the whole plant) which have been collected for further storage and/or further use.

"Harvested seeds" refers to seeds harvested from a line or variety, e.g., produced after self-fertilization or cross-fertilization and collected.

"Harvested leaves" as used herein refers to spinach leaves, i.e., the plant without the root system, for example substantially all (harvested) leaves.

"Progeny" or "progenies" or "descendants" as used herein refers to offspring, or the first and all further descendants derived from (obtainable from) (derivable from or obtained from) a plant of the invention that comprises (retains) the RPF11 resistance gene in homozygous or heterozygous form and/or the RPF11 resistance phenotype described herein. Progeny may be derived by regeneration of cell culture or tissue culture, or parts of a plant, or selfing of a plant, or by producing seeds of a plant. In further embodiments, progeny may also encompass spinach plants derived from crossing of at least one spinach plant with another spinach plant of the same or another variety or (breeding) line, and/or backcrossing, and/or inserting of a locus into a plant and/or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Also double haploid plants are progeny.

"Plant line" is for example a breeding line which can be used to develop one or more varieties.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"Hybrid" refers to the seeds harvested from crossing one plant line or variety with another plant line or variety, and the plants or plant parts grown from said seeds.

"F1 hybrid" plant (or F1 hybrid seed) is the generation obtained from crossing two non-isogenic inbred parent lines. Thus, F1 hybrid seeds are seeds from which F1 hybrid plants grow.

An "interspecific hybrid" refers to a hybrid produced from crossing a plant of one species, e.g. *S. oleracia*, with a plant of another species, e.g. *S. tetrandra* or *S. turkestanica*.

"Crossing" refers to the mating of two parent plants. Equally "Cross-pollination" refers to fertilization by the union of two gametes from different plants.

"Selfing" refers to the self-pollination of a plant, i.e. to the union of gametes from the same plant.

"Backcrossing" refers to a breeding method by which a (single) trait, such as Pfs resistance conferred by the RPF11 resistance gene, can be transferred from one genetic background (also referred to as "donor"; generally but not necessarily this is an inferior genetic background) into another genetic background (also referred to as "recurrent parent"; generally but not necessarily this is a superior genetic background). An offspring of a cross (e.g. an F1 plant obtained by crossing a wild spinach or wild relative of spinach with a cultivated spinach; or an F2 plant or F3 plant, etc., obtained from selfing the F1) is "backcrossed" to the parent with the superior genetic background, e.g. to the cultivated parent. After repeated backcrossing, the trait of the donor genetic background, e.g. the RPF11 gene, will have been incorporated into the recurrent genetic background. The terms "gene converted" or "conversion plant" or "single locus conversion" in this context refer to plants which are developed by backcrossing wherein essentially all of the desired morphological and/or physiological characteristics of the recurrent parent are recovered in addition to the one or more genes (e.g. the RPF11 resistance gene) transferred from the donor parent.

The term "traditional breeding techniques" encompasses herein crossing, backcrossing, selfing, selection, chromosome doubling, double haploid production, embryo rescue, the use of bridge species, protoplast fusion, marker assisted selection, mutation breeding etc. as known to the breeder (i.e. methods other than genetic modification/transformation/transgenic methods), by which, for example, the RPF11-resistance gene can be obtained, identified, selected, and/or transferred.

"Regeneration" refers to the development of a plant from in vitro cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting off) leaf, pollen, embryo, cotyledon, hypocotyl, cells, protoplasts, meristematic cell, root, root tip, pistil, anther, flower, shoot tip, shoot, stem, fruit, and petiole. When a whole plant is regenerated by vegetative propagation, it is also referred to as a "vegetative propagation" or a "vegetatively propagated plant".

"Single locus converted (conversion) plant" refers to plants which are developed by plant breeding techniques comprising or consisting of backcrossing, wherein essentially all of the desired morphological and/or physiological characteristics of a spinach plant are recovered in addition to the characteristics of the single locus (e.g. the locus comprising the RPF11 gene) having been transferred into the plant via the backcrossing technique and/or by genetic transformation.

"Transgene" or "chimeric gene" refers to a genetic locus comprising a DNA sequence which has been introduced into the genome of a spinach plant by transformation. A plant comprising a transgene stably integrated into its genome is referred to as "transgenic plant".

"Pfs" or "*Peronospora farinosa*" or "downy mildew" refers to races of the oomycete *Peronospora farinosa* f. sp. *spinaciae*. Pfs1-Pfs14 refer to the officially recognized races, which can be differentiated on the differential hosts of spinach and which can be obtained from the Naktuinbouw, P.O. Box 40, 2370 AA Roelofarendsveen, The Netherlands, or via references provided by the ISF (International Seed Federation).

"Differential hosts" or "differentials" refers to the differential hosts of spinach for distinguishing Pfs races 1-14, which can be obtained from the Naktuinbouw, P.O. Box 40, 2370 AA Roelofarendsveen, The Netherlands, or via references provided by the ISF (International Seed Federation).

"UA4712" refers to a pathogenic isolate of Pfs which has not yet been officially recognized as a new Pfs race. It is described by Correl and Koike, 2013, Race diversity and the biology of the spinach downy mildew pathogen, CLGRB Annual Report, Apr. 1, 2012 to Mar. 31, 2013.

A "Pfs resistant plant" or "downy mildew resistant plant" or a plant having "Pfs resistance" or a "Pfs resistant phenotype" refers to a spinach plant which is resistant against one or more pathogenic races (and pathogenic isolates) of Pfs, as determined in a qualitative resistance assay under controlled environmental conditions. In such a resistance assay a plurality of plants (e.g. at least 2 replicates of at least 10 plants) of a genotype, are inoculated with a sporangial suspension of the race or isolate and incubated under suitable conditions. After a suitable incubation period (e.g. 7, 8, 9, 10, 11 or more days after inoculation) the plants are evaluated for symptoms. Susceptible controls should show sporulation at the time of symptom evaluation. Any plant showing sporulation on the cotyledons (and/or on the true leaf/leaves) is considered "susceptible", while any plant not showing any sporulation on the cotyledons (and/or on the true leaf/leaves) is considered "resistant". A plant genotype with more than 85% of the inoculated plants (preferably more than 95%) being classified as "resistant" plant is considered to a resistant against the race or isolate. In the test >85% of inoculated plants (preferably more than 95% of plants) of the susceptible control plant, such as cultivar Viroflay, should show sporulation. Suitable tests are described herein in the Examples, or in Irish et al. 2007 (Plant Disease Vol 91 No. 11, in Materials and Methods on page 1392-1394), or in Correll et al. 2010, "Guidelines for Spinach Downy Mildew: *Peronospora ferinosa* f. sp. *spinaciae* (Pfs)" found on the website of the ISF (International Seed Federation).

"RPF11" refers herein to a single, dominant Pfs resistance gene, which confers Pfs resistance (as defined above) against at least races 7-14, and optionally against UA4712 (and optionally against new pathogenic isolates). In one embodiment RPF11 refers to a resistance gene which confers resistance against at least races 7-14 and optionally further against one or more of races 1-6 (e.g. against at least races 1, 2, 5 and 6), and/or optionally against UA4712 (and optionally against new pathogenic isolates). The resistance is conferred when the gene is in homozygous or heterozygous form. The resistance phenotype is also referred to herein as the "Pfs resistance phenotype conferred by the RPF11 gene".

The term "locus" (loci plural) means a specific place or places or a site on a chromosome where for example a gene (e.g. the RPF11 gene) or genetic marker is found. In spinach according to the invention the resistance locus comprising the RPF11 gene is introgressed from a wild spinach or wild relative of spinach.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Allelism test" refers to a genetic test whereby it can be tested whether a phenotype, such as Pfs resistance, seen in two plants, is determined by the same gene or by different genes. For example, the plants to be tested are crossed with each other, the F1 is selfed and the segregation of the phenotypes amongst the F2 progeny is determined. Other segregating populations can equally be made (e.g. backcross populations). The ratio of segregation of the phenotype indicates if the genes are allelic (alleles of the same gene) or non-allelic (different, independent genes).

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In spinach, wild spinach or wild relatives of spinach are often used to introgress fragments of the wild genome into the genome of cultivated spinach. Such a spinach plant thus has a "genome of *Spinacia oleracea*", but comprises in the genome a fragment of a wild spinach or spinach relative. It is understood that the term "introgression fragment" never includes a whole chromosome, but only a part of a chromosome. The introgression fragment can be large, e.g. even half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

"Physical distance" between loci (e.g. between molecular markers and/or between phenotypic markers) on the same chromosome is the actual physical distance expressed in base pairs (bp), kilo base pairs (kb) or megabase pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

A genetic element, a locus, an introgression fragment or a gene or allele conferring a trait (such as resistance against Pfs) is said to be "obtainable from" or can be "obtained from" or "derivable from" or can be "derived from" or "as present in" or "as found in" a plant or seed if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like.

The term "traditional breeding techniques" encompasses herein crossing, backcrossing, selfing, selection, chromosome doubling, double haploid production, embryo rescue, the use of bridge species, protoplast fusion, marker assisted selection, mutation breeding etc. as known to the breeder (i.e. methods other than genetic modification/transformation/transgenic methods), by which, for example, the RPF11 gene can be obtained, identified, selected, and/or transferred.

DETAILED DESCRIPTION OF THE INVENTION

Plants and Methods of the Invention

The invention provides a spinach plant comprising resistance against at least *Peronospora farinosa* races 7-14, wherein said resistance is conferred by a single gene. The gene, designated herein RPF11 (for Resistance to *Peronospora Farinosa* 11) further optionally confers resistance against one or more of *Peronospora farinosa* races 1-6. In one aspect the RPF11 gene, therefore, confers resistance against all currently known pathogenic Pfs races, races 1-14, when in homozygous or heterozygous form in the plant. In another aspect the RPF11 gene confers at least resistance against pathogenic Pfs races 1 and 2 and 5 to 14 when in homozygous or heterozygous form in the plant. In yet another aspect the RPF11 gene confers at least resistance against pathogenic Pfs races 7-14, when in homozygous or heterozygous form in the plant; and optionally also against one or more of races 1-6 Optionally, the resistance gene also confers resistance against one or more pathogenic isolates of Pfs, such as isolate UA4712 or other isolates, including future isolates or races which develop in the field due to large scale uses of Pfs resistant spinach varieties. Thus, in another aspect the RPF11 gene confers resistance against at least pathogenic Pfs races 7-14 and against UA4712, when in homozygous or heterozygous form in the plant.

The RPF11 gene is a single, dominant resistance gene, i.e. when a plant comprising RPF11 in homozygous form (such as a plant grown from seed deposited under accession number NCIMB 42158) is crossed with a susceptible plant, such as variety Viroflay, the F2 progeny will segregate in a 3 (resistant):1 (susceptible) ratio.

Such a single, dominant resistance gene, which is effective against all, or almost all, know pathogenic races, is of great advantage in generating resistant spinach varieties. Up to date resistance genes with complementary resistance phenotypes were stacked to provide resistance against several races. For example, the F1 hybrid variety *Andromeda* is a stack of two resistance genes, one inherited from the female parent and one from the male parent line.

A representative sample of seeds of a spinach line comprising the RPF11 gene in homozygous form has been deposited under Accession number NCIMB 42158.

In one aspect of the invention a spinach plant comprising the RPF11 resistance gene is obtainable by (or obtained by, or derivable from, or derived from) crossing a spinach plant grown from seeds deposited under accession number NCIMB 42158, with another spinach plant, for example with a spinach plant lacking Pfs resistance genes (a susceptible plant) or with a spinach plant comprising one or more different Pfs resistance genes. Thus, in one aspect a spinach plant comprising resistance against at least *Peronospora farinose* races 7-14 is provided wherein the resistance is conferred by a single dominant gene, called RPF11, wherein the RPF11 gene is the gene as present in seeds deposited under NCIMB41258 or progeny thereof.

In one embodiment of the invention, the RPF11 gene is, therefore the gene as found in plants (or plant parts) grown from seeds deposited under accession number NCIMB 42158 or in progeny of such plants, such as plants obtained by selfing NCIMB 42158 or by crossing NCIMB 42158 with another spinach plant to obtain progeny and by retaining the resistance gene in the progeny (e.g. using phenotypic and/or molecular methods to identify or select progeny containing the RPF11 gene).

Therefore in one embodiment of the invention a spinach plant is provided comprising resistance against *Peronospora farinosa* races 7-14, wherein said resistance is conferred by a single gene, wherein said gene is the gene as found in (or as obtainable from) seeds deposited under accession number NCIMB42158, e.g. by crossing a plant grown from seeds of accession number NCIMB42158 with another spinach plant. In one aspect the (dominant) gene is in homozygous or heterozygous form.

In fact, the RPF11 gene (and the Pfs resistance phenotype conferred by the gene), can be transferred from the seeds deposited under NCIMB 42158, or from progeny of said seeds, into any spinach line or variety by traditional breeding techniques and can confer race 7-14 resistance, optionally further one or more of race 1-6 resistance (e.g. at least race 1, 2, 5 and 6), and/or UA4712 resistance (and optionally resistance against new pathogenic isolates) onto another spinach plant. Thus, for example, a spinach plant of the invention can be used as male or female parent in a cross with another spinach plant, and progeny, such as F1, F2, F3, or further generations of selfing and/or backcross progeny (e.g. BC1, BC2, BC1S1, BC2S1, BC1S2, etc.) can be identified and selected, whereby the progeny comprise the same Pfs resistance phenotype as the initial plant of the invention. Selection of progeny for the presence of the RPF11 gene (and the Pfs resistance phenotype conferred by the gene) can, therefore, be carried out using a disease resistance assay as described herein, whereby resistance against one or more (or all) of the Pfs races is tested in the progeny.

It is not always necessary to test progeny plants for resistance against all the Pfs races, as the transfer of resistance against one race is indicative of the transfer of the gene and the resistance against the other races is automatically transferred with the gene. Thus, if the second parent in the cross lacks resistance against a particular Pfs race, then selection of progeny which are resistant against that race is sufficient to indicate the transfer of the RPF11 gene.

Therefore, in one aspect of the invention a spinach is provided comprising resistance against at least *Peronospora farinosa* races 7-14, optionally further comprising resistance against one or more of races 1-6 and/or optionally further comprising resistance against isolate UA4712 and optionally new pathogenic isolates. Optionally the RPF11 gene also provides resistance against one or more races selected from the group consisting of race 1, 2, 3, 4, 5 and 6, especially at least races 1, 2, 5 and 6. In a further embodiment the spinach plant comprises resistance against at least Pfs races 7-14 and UA4712 and optionally further new pathogenic isolates. In yet a different embodiment the spinach plant comprises resistance against at least one or more Pfs races selected from the group of 1, 2, 3, 4, 5 and 6 (for example at least against 1, 2, 5 and 6), and additionally against 7 to 14 and UA4712 and optionally further new pathogenic isolates. When reference is made elsewhere herein to 'resistance against Pfs races 7-14', or to 'resistance against at least races Pfs 7-14', it is understood that the other resistances conferred by the RPF11 gene (as described above) are also encompassed in these or different embodiments.

Whether a spinach plant genotype (i.e. a spinach line or variety) comprises resistance against one or more Pfs races or isolates can be tested using qualitative disease resistance assays under controlled environment conditions. Different protocols of such assays exist and can be used by the person skilled in the art. In short, seedlings of a plurality of plants of the plant genotype to be tested (e.g. at least 6, 7, 8, 9, 10, 11, 12, 13, 14, 15, 16, 17, 18, 19, 20, or more) are inoculated with inoculum of the Pfs race and the seedlings are incubated under conditions which are favorable to the pathogen. Several days after incubation, the plants are assessed for infection symptoms, especially sporulation on the cotyledons and/or leaves (e.g. first true leaf), and each plant is categorized as "resistant" (showing no signs of sporulation) or "susceptible" (showing sporulation). If a certain percentage of all plants of a genotype are classified as "resistant", e.g. more than about 85%, 90%, 95%, 98%, 99% (or even 100%), then the spinach plant genotype is resistant to the race tested. Obviously, also one or more control plants (e.g. a susceptible line or variety, a resistant line or variety) should be included in the assay using the same treatment(s) and environmental conditions, to ensure that the assay works as expected.

Alternatively or in addition to the phenotypic assay, selection or identification of a spinach plant (e.g. a progeny plant) comprising the RPF11 gene of the invention may be achieved by detecting one or more molecular markers linked to the RPF11 gene or locus. This aspect will be described elsewhere herein.

In one of the embodiments of the invention, the spinach plant is an inbred line, especially an inbred line which can be used as a parent for F1 hybrid seed production. In another embodiment of the invention, the spinach plant is a hybrid, especially an F1 hybrid. An F1 hybrid may be generated by crossing a first inbred parent line which comprises the RPF11 gene, preferably in homozygous form, with a second inbred parent line. The first inbred parent line may be a line developed from using seeds deposited under NCIMB 42158 or from progeny of plants grown from these seeds, whereby the progeny retain the Pfs resistance phenotype (and the RPF11 gene).

The second inbred parent line may be any spinach line, i.e. it may completely lack Pfs resistance, or it may comprise a different Pfs resistance gene (and different resistance phenotype) or it may also comprise the RPF11 gene.

As the RPF11 gene is dominant, a hybrid spinach plant comprising only one copy of the RPF11 gene will show the resistance phenotype conferred by the gene.

As mentioned, the spinach plant according to the invention may be any type of spinach, as the RPF11 gene can be easily transferred into any spinach line or variety. For example, the spinach plant may be a savoy type, a semi-savoy type or flat- or smooth leaved spinach. In other words, the RPF11 gene can be introduced into any other spinach plant by introgression from a plant grown from seeds of which a representative sample was deposited under NCIMB 42158, or any spinach plant derived therefrom and comprising the RPF11 gene. The deposited seeds are therefore a source of the RPF11 resistance gene of the invention, as are spinach plants not directly obtained from the deposit, but for example indirectly obtained (e.g. later released commercial varieties) and which contain the RPF11 gene of the invention. Other sources of the RPF11 gene may be identified, e.g. in wild spinach or wild relatives of spinach and e.g. an allelism test may be used to determine whether another dominant gene, conferring the same Pfs resistance phenotype as the plant of the invention (or as progeny thereof), is the same gene or a different gene. Alternative methods to determine whether another gene is the same gene include the development of molecular markers linked to the RPF11 gene of the invention and analyzing whether the markers also occur in plants comprising the other gene.

The RPF11 gene was identified in wild material from a genebank and was introduced through backcrossing into *S. oleracea*. In one aspect, therefore, a spinach plant is provided comprising resistance against at least Pfs races 7-14, optionally further against one or more of races 1 to 6, and/or optionally further against UA4712 and/or new pathogenic isolates, wherein said resistance against *Peronospora farinosa* is conferred by an introgression fragment from wild spinach or from a wild relative of spinach, wherein the wild relative is selected from *Spinacia tetranda* and *Spinacia turkestanica*.

In one embodiment, the introgression fragment is the fragment as found in (and as obtainable from; or obtained from; or derivable from; or derived from) spinach seeds, a representative sample of seeds having been deposited under accession number NCIMB 42158. The fragment can be identified by various methods, such as chromosome painting or sequencing the spinach genome and identifying chromosome parts which are introgressions from wild spinach or wild relatives of spinach. The fragment can also be identified by one or more molecular markers (e.g. SNP markers, AFLP markers, RFLP markers, etc.), especially molecular markers which are polymorphic between cultivated spinach and the wild introgression fragment. Thus, in one aspect the plant comprising the RPF11 gene as found in NCIMB 42158 comprises the same RPF11 markers or genomic gene sequence or introgression fragment as found in NCIMB42158 (or in progeny thereof).

In another embodiment, the introgression fragment is derived from the fragment as found in spinach seeds, a representative sample of seeds having been deposited under accession number NCIMB 42158, whereby the introgression fragment is shorter but retains the RPF11 gene (and the Pfs resistance phenotype conferred by the gene). Spinach plants comprising such shorter introgression fragments can be generated by crossing a plant of the invention with another spinach plant and selecting recombinant progeny which retain the resistance phenotype conferred by the RPF11 gene, but which contain a shorter introgression fragment.

In one aspect a method is provided for generating a spinach plant comprising resistance against at least Pfs races 7-14, optionally further against one or more of races 1-6 (such as at least races 1, 2, 5 and 6), and/or optionally against UA4712, comprising the steps of:
  a) Providing a spinach plant comprising resistance against at least Pfs races 7-14, optionally further against one or more of races 1-6, and/or optionally against UA4712;
  b) Crossing said spinach plant with another spinach plant to produce F1 seeds;
  c) Optionally selfing the plants grown from F1 seeds one or more times to produce F2, F3 or further generation selfing progeny;
  d) Identifying (or selecting) spinach plants grown from F1, F2, F3 or further generation selfing progeny which have resistance against at least Pfs races 7-14, optionally further against one or more of races 1-6, and/or optionally against UA4712;
  e) Optionally crossing said identified (or selected) F1 progeny or selfing progeny to the spinach plant of step b), to produce a backcross progeny;
  f) Optionally selecting backcross progeny comprising resistance against at least Pfs races 7-14, optionally further against one or more of races 1-6, and/or optionally against UA4712.

In another embodiment a method for generating a spinach plant comprising resistance against at least *Peronospora farinosa* races 7-14 (optionally further against one or more of races 1-6 such as at least races 1, 2, 5 and 6, and/or optionally against UA4712) is provided comprises the steps of:
  a) Providing a spinach plant comprising an introgression fragment obtainable from (or as in) accession NCIMB 42158, which introgression fragment confers resistance against at least *Peronospora farinosa* races 7-14 (optionally further against one or more of races 1-6, and/or optionally against UA4712);
  b) Crossing said spinach plant with another spinach plant, for example with a spinach plant which is susceptible against one or more of *Peronospora farinosa* races 7-14, to produce F1 seeds;
  c) Optionally selfing the plants grown from F1 seeds one or more times to produce F2, F3 or further generation selfing progeny;
  d) Identifying spinach plants grown from F1, F2, F3 or further generation selfing progeny which have resistance against at least *Peronospora farinosa* races 7-14 (optionally further against one or more of races 1-6, and/or optionally against UA4712) and/or which comprise the introgression fragment or a resistance-conferring part of the introgression fragment;
  e) Optionally crossing said identified F1 progeny or selfing progeny to the spinach plant of step b), to produce a backcross progeny;
  f) Optionally selecting backcross progeny which comprises resistance against at least *Peronospora farinosa* races 7-14 (optionally further against one or more of races 1-6, and/or optionally against UA4712) and/or which comprise the introgression fragment or a resistance-conferring part of the introgression fragment.

Regarding both methods, the following is encompassed herein.

In one aspect the plant of a) comprises the RPF11 gene as found in seeds deposited under accession number NCIMB 42158. The spinach plant may be the plant grown from the seeds of the deposit or any spinach plant made using, or having used, the seed deposit and which retains the Pfs resistance phenotype (and the gene conferring it). This includes commercial spinach varieties which were made using the seed deposit. Thus, the spinach plant of a) comprises the RPF11 gene according to the invention, e.g. as found in (or as obtainable from; obtained from; derivable from; derived from) NCIMB 42158. The plant in a) may therefore be a plant grown from seeds, a representative sample of which has been deposited under NCIMB42158 (comprising RPF11 in homozygous form) or from progeny of such seeds which retain the RPF11 gene and phenotype.

Selections (or identification) in step d) and/or f) may be made based on the phenotype (i.e. using a Pfs resistance assay) and/or based on molecular methods, such as detection of molecular markers linked to the RPF11 gene or locus, or other methods such as sequencing.

In the methods above, the spinach plant of step (a) preferably comprises the RPF11 gene (i.e. the introgression fragment comprising the RPF11 gene) in homozygous form.

In step b) the spinach plant is, in one aspect, crossed with a spinach plant which is susceptible against at least one of the Pfs races against which the plant of a) is resistant. If the second parent in b) is a spinach plant which is susceptible against at least one of the Pfs races against which the plant of a) is resistant, then the selection in step (d) and/or (f) may be based on selecting plants which now have resistance against that race.

Steps e) and f) may be repeated one or more times.

In the above methods also plants can be selected and/or identified which retain the Pfs resistance phenotype conferred by the RPF11 gene, but which have a smaller introgression fragment. This can have advantages, as negative traits coupled to the wild introgression fragment can thereby be removed. Initial introgression fragments from wild sources can be quite large, e.g. 20 Mb or 30 Mb. It is therefore preferred to reduce the size of the introgression fragment by recombination and to select plants comprising smaller introgression fragments, but which retain the resistance-conferring part. So, spinach with all sizes of introgression fragments originating from (or derived from; or derivable from; or obtained from; or obtainable from) seeds deposited under accession number NCIMB 42158 are included herein, as long as the Pfs resistance conferring part (i.e. the RPF11 gene) is retained in the spinach plant. As mentioned, the presence can be tested/selected phenotypically and/or using molecular methods known in the art.

Also plants obtainable or obtained by any of the above methods are embodiments of the invention.

The plants according to the invention may be any cultivated spinach, e.g. savoy, semi-savoy, flat- or smooth leaved spinach. They may be inbred lines, F1 hybrids, double haploids, transgenic plants, mutant plants, a single locus converted plant comprising the RPF11 gene, etc.

Plants of the invention can be used to generate progeny, which have or retain the Pfs resistance phenotype as obtainable from (as present in; as derivable from; as obtained or derived from) seeds deposited under accession number NCIMB 42158. To generate progeny, a spinach according to the invention can be selfed and/or crossed one or more times with another spinach plant and seeds can be collected. The presence of the RPF11 gene in the progeny plants can be determined (i.e. progeny plants comprising the RPF11 gene can be identified/selected) by the Pfs resistance phenotype and/or molecular methods, such as molecular markers (e.g. SNP markers) closely linked to the RPF11 gene or locus.

Also seeds from which the plants of the invention can be grown are provided.

In one embodiment, the use of a spinach plant, of which representative seeds have been deposited under accession number NCIMB 42158, or progeny thereof (e.g. obtained by selfing), for generating a spinach plant comprising Pfs resistance against at least *Peronospora farinosa* races 7-14 (optionally further against one or more of races 1-6, and/or optionally against UA4712) is provided.

In another embodiment, the use of a spinach plant comprising resistance against at least *Peronospora farinosa* races 7-14 conferred by an introgression fragment obtainable from (or as present in; as derivable from; as obtained or derived from) seeds deposited under accession number NCIMB 42158, or from progeny thereof (e.g. obtained by selfing), for generating spinach plant comprising resistance against at least *Peronospora farinosa* races 7-14 (optionally further against one or more of races 1-6, and/or optionally against UA4712) is provided.

It is noted that also allelism tests can be used to determine whether the resistance gene in a spinach plant is the same gene or a different gene as the RPF11 gene as present in NCIMB42158 (or in progeny thereof). So, NCIMB42158 (or progeny) can be crossed with another spinach plant comprising the same resistance phenotype and in progeny of such a cross one can determine in which ratios the phenotype segregates. So in one aspect a spinach plant is provided comprising resistance against *P. ferinosa* races 7-14, wherein said resistance gene conferring said resistance phenotype is the dominant RPF11 gene as present in NCIMB42158 (or progeny thereof), i.e. is allelic to RPF11 (is a different allele of the RPF11 gene found in NCIMB42158), as determinable in an allelism test. Allelism tests for dominant genes are known in the art and are e.g. described in Hibberd et al. 1987 (Phytopathology 77: 1304-1307).

Seeds

Also seeds from which any of the plants of the invention can be grown are provided, as are containers or packages containing or comprising such seeds. Seeds can be distinguished from other seeds due to the presence of the RPF11 resistance gene, either phenotypically (based on plants having the RPF11 resistance phenotype) and/or using molecular methods.

In one aspect, seeds are packaged into small and/or large containers (e.g., bags, cartons, cans, etc.). The seeds may be pelleted prior to packing (to form pills or pellets) and/or treated with various compounds, such as seed coatings.

Seed pelleting can be combined with film coating (Halmer, P. 2000. Commercial seed treatment technology. In: Seed technology and its biological basis. Eds: Black, M. and Bewley, J. D., pages 257-286). Pelleting creates round or rounded shapes, which are easily sown with modern sowing machines. A pelleting mixture typically contains seeds and at least glue and filler material. The latter could be, for example, clay, mica, chalk or cellulose. In addition, certain additives can be included to improve particular properties of the pellet, e.g., a seed treatment formulation comprising at least one insecticidal, acaricidal, nematicidal or fungicidal compound can be added directly into the pelleting mixture or in separate layers. A seed treatment formulation can include one of these types of compounds only, a mixture of two or more of the same type of compounds or a mixture of one or more of the same type of compounds with at least one other insecticide, acaricide, nematicide or fungicide.

Formulations especially suitable for the application as a seed treatment can be added to the seed in the form of a film coating including also the possibility of using the coating in or on a pellet, as well as including the seed treatment formulation directly into the pellet mixture. Characteristically, a film coating is a uniform, dust-free, water permeable film, evenly covering the surface of all individual seeds (Halmer, P. 2000. Commercial seed treatment technology. In: Seed technology and its biological basis. Eds: Black, M. and Bewley, J. D., pages 257-286). Besides the formulation, the coating mixture generally also contains other ingredients such as water, glue (typically a polymer), filler materials, pigments and certain additives to improve particular properties of the coating. Several coatings can be combined on a single seed.

In addition, several combinations with film coating are possible: the film coating can be added on the outside of the pellet, in between two layers of pelleting material, and directly on the seed before the pelleting material is added. Also more than 1 film coating layer can be incorporated in a single pellet. A special type of pelleting is encrusting. This technique uses less filler material, and the result is a 'mini-pellet'.

Seeds may also be primed. Spinach is often primed. Priming is a water-based process that is performed on seeds to increase uniformity of germination and emergence from the soil, and thus enhance vegetable stand establishment. Priming decreases the time span between the emergence of the first and the last seedlings. Methods how to prime spinach seeds are well known in the art (see, e.g., Chen et al. 2010, Seed Sci. & Technol. 38: 45-57).

Plant Parts and Vegetative Reproductions

In a further aspect plant parts, obtained from (obtainable from) a plant of the invention are provided herein, and containers or packages comprising said plant parts.

In a preferred embodiment the plant parts are leaves of spinach plants of the invention, preferably harvested leaves, or parts of these. Leaves may be loose, bunched, fresh (e.g. in bags), frozen, blanched or boiled. Leaves may be fresh or processed, they may be part of food or feed products, such as salads, etc.

Other plant parts, of plants of the invention, include stems, cuttings, petioles, cotyledons, flowers, anthers, pollen, ovaries, roots, root tips, protoplasts, callus, microspores, stalks, ovules, shoots, seeds, embryos, embryo sacs, cells, meristems, buds etc.

Seeds include for example seeds produced on the plant of the invention after selfpollination or seed produced after cross-pollination, e.g. pollination of a plant of the invention with pollen from another spinach plant or pollination of another spinach plant with pollen of a plant of the invention.

In a further aspect, the plant part is a plant cell. In still a further aspect, the plant part is a non-regenerable cell or a regenerable cell. In another aspect the plant cell is a somatic cell.

A non-regenerable cell is a cell which cannot be regenerated into a whole plant through in vitro culture, but the non-regenerable cell may be in a plant or plant part (e.g. leaves) of the invention.

In a further aspect the plant cell is a reproductive cell, such as an ovule or pollen. These cells are haploid. When they are regenerated into whole plants, they comprise the haploid genome of the starting plant. If chromosome doubling occurs (e.g. through chemical treatment), a double haploid plant can be regenerated. In one aspect the plant of the invention, comprising the RPF11 resistance gene is a haploid or a double haploid spinach plant.

Moreover, there is provided a in vitro cell culture or tissue culture of spinach plants of the invention in which the cell- or tissue culture is derived from a plant parts described above, such as, for example and without limitation, leaves, pollen, embryos, cotyledon, hypocotyls, callus, meristematic cells, roots, root tips, anthers, flowers, seeds or stems, somatic cells, reproductive cells.

Also provided are spinach plants regenerated from the above-described plant parts, or regenerated from the above-described cell or tissue cultures, said regenerated plant having a Pfs resistance phenotype (as conferred by the RPF11 gene), i.e. retains the RPF11 gene (or the introgression fragment comprising the RPF11 gene) of the invention. These plants can also be referred to as vegetative propagations of plants of the invention.

Also provided are harvested leaves of plants of the invention and packages comprising a plurality of leaves of plants of the invention. These leaves thus comprise the RPF11 gene of the invention, detectable by e.g. linked molecular markers or phenotypically (for the originally used whole plant and/or regenerated plant).

The invention also provides for a food or feed product comprising or consisting of a plant part described herein. The food or feed product may be fresh or processed, e.g., canned, steamed, boiled, fried, blanched and/or frozen etc. Examples are salad or salad mixtures comprising leaves or parts of leaves of plants of the invention.

A spinach plant of the invention or a progeny thereof retaining the Pfs resistance phenotype conferred by the RPF11 gene and/or retaining the introgression fragment comprising the RPF11 gene, as present in NCIMB 42158, and parts of the afore-mentioned plants, can be suitably packed for, e.g., transport, and/or sold fresh. Such parts encompass any cells, tissues and organs obtainable from the seedlings or plants, such as but not limited to: leaves, cuttings, pollen, parts of leaves, and the like.

Leaves may be harvested immature, as baby-leaf or baby spinach, or mature. A plant, plants or parts thereof may be packed in a container (e.g., bags, cartons, cans, etc.) alone or together with other plants or materials. Parts can be stored and/or processed further. Encompassed are therefore also food or feed products comprising one or more of such parts, such leaves or parts thereof obtainable from a plant of the invention, a progeny thereof and parts of the afore-mentioned plants. For example, containers such as cans, boxes, crates, bags, cartons, Modified Atmosphere Packaging, films (e.g. biodegradable films), etc. comprising plant parts of plants (fresh and/or processed) of the invention are also provided herein.

Plants and Progeny

In another embodiment, plants and parts of spinach plants of the invention, and progeny of spinach plants of the invention are provided, e.g., grown from seeds, produced by sexual or vegetative reproduction, regenerated from the above-described plant parts, or regenerated from cell or tissue culture, in which the reproduced (seed propagated or vegetatively propagated) plant comprises resistance against at least Pfs races 7-14, optionally further against one or more of races 1-6, and/or optionally against UA4712 (as conferred by the RPF11 gene).

As mentioned before, whether or not a plant, progeny or vegetative propagation comprises the Pfs resistance phenotype as conferred by the RPF11 gene can be tested phenotypically using e.g. the Pfs disease resistance assays as described above or in the Examples; and/or using molecular techniques such as molecular marker analysis, DNA sequencing (e.g. whole genome sequencing to identify the wild introgression), chromosome painting, etc.

In one embodiment, the RPF11 resistance gene obtainable from (obtained from; as found in) plants deposited under NCIMB 42158, or progeny thereof, can be combined with other *Peronospora farinosa* resistance genes or resistance loci (e.g. RPF1-RPF6, R6, etc.) or with other traits, such resistance against bacteria (e.g. *Pseudomonas syringae* pv. *spinacea; Erivinia carotovora*), fungi (e.g. *Albugo occidentalis, Colletotrichum dematium* f. sp. *spinaciae; Stemphylium botryosum* f. sp. *spinacia*), viruses (e.g. viruses causing curly top disease) or nematodes. This can be done by traditional breeding techniques, e.g. by backcrossing in order to introduce one or more traits into a plant of the invention or in order to introduce the RPF11 gene of a plant of the invention into another spinach plant comprising such one or more additional traits. Thus, in one aspect a plant of the invention is used as a donor of the RPF11 gene, while in another aspect a plant of the invention is used as recipient of one or more other traits.

Furthermore, the invention provides for progeny comprising or retaining the Pfs resistance phenotype (conferred by the RPF11 gene), such as progeny obtained by, e.g., selfing one or more times and/or cross-pollinating a plant of the invention with another spinach plant of a different variety or breeding line, or with a spinach plant of the invention one or more times. In particular, the invention provides for progeny that retain the RPF11 gene (conferring the Pfs resistance phenotype) of (as found in) NCIMB 42158. In one aspect the invention provides for a progeny plant comprising the RPF11 resistance, such as a progeny plant that is produced from a spinach plant comprising the RPF11 resistance by one or more methods selected from the group consisting of: selfing, crossing, mutation, double haploid production or transformation.

Mutation may be spontaneous mutations or human induced mutations or somaclonal mutations.

In one embodiment, plants or seeds of the invention may also be mutated (by e.g. irradiation, chemical mutagenesis, heat treatment, TILLING, etc.) and/or mutated seeds or plants may be selected (e.g. natural variants, somaclonal variants, etc.) in order to change one or more characteristics of the plants. Similarly, plants of the invention may be transformed and regenerated, whereby one or more chimeric genes are introduced into the plants.

Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into the plants, or progeny thereof, by transforming a plant of the invention or progeny thereof with a transgene that confers the desired trait, wherein the transformed plant retains the RPF11 gene and the Pfs resistance phenotype conferred by it and contains the desired trait.

The RPF11 gene or allele may be transferred to progeny by further breeding. In one aspect progeny are $F_1$ progeny obtained by crossing a plant of the invention with another plant or S1 progeny obtained by selfing a plant of the invention. Also encompassed are F2 progeny obtained by selfing the $F_1$ plants, or further generation progeny. "Further breeding" encompasses traditional breeding techniques (e.g., selfing, crossing, backcrossing), marker assisted breeding, and/or mutation breeding. In one embodiment, the progeny have the Pfs resistance phenotype of NCIMB 42158 and comprising the RPF11 gene (or introgression comprising the gene or the reduced size introgression fragment comprising the RPF11 gene) obtainable/obtained from (or as found in) NCIMB 42158.

In one aspect haploid plants and/or double haploid plants of plant of the invention are encompassed herein, which comprise resistance against at least *Peronospora farinosa* races 7-14 (optionally further against one or more of races 1-6, and/or optionally against UA4712), as conferred by the RPF11 gene or by the introgression fragment comprising the RPF11 gene. Haploid and double haploid (DH) plants can for example be produced by anther or microspore culture and regeneration into a whole plant. For DH production chromosome doubling may be induced using known methods, such as colchicine treatment or the like. So, in one aspect a spinach plant is provided, comprising Pfs resistance phenotype as described, wherein the plant is a double haploid plant.

In another embodiment the invention relates to a method for producing spinach seed, comprising crossing a plant of the invention with itself or a different spinach plant and harvesting the resulting seed. In a further embodiment the invention relates to seed produced according to this method and/or a spinach plant produced by growing such seed. Thus, a plant of the invention may be used as male and/or female parent, in the production of spinach seeds, whereby the plants grown from said seeds comprise at least *Peronospora farinosa* races 7-14 (optionally further against one or more of races 1-6, and/or optionally against UA4712), due to the presence of the RPF11 gene.

Thus, in one aspect progeny of a spinach plant of the invention are provided, wherein the progeny plant is produced by selfing, crossing, mutation, double haploid production or transformation and wherein the progeny retain the RPF11 resistance gene (and phenotype conferred by it) described herein, i.e. obtainable by crossing a spinach plant, grown from seeds deposited under accession number NCIMB 42158, with another spinach plant. In other words, the resistance gene or locus (or introgression fragment comprising the gene or locus) as present in/found in/as derived from (or as derivable from) seed deposit NCIMB 42158 is retained in the progeny plants.

Molecular markers may also be used to aid in the identification of the plants (or plant parts or nucleic acids obtained therefrom) containing the RPF11 resistance gene or locus or allele(s). For example, one can develop one or more suitable molecular markers which are closely genetically (and preferably also physically) linked to the RPF11 resistance gene, locus or allele. This can be done by crossing a resistant spinach plant (comprising RPF11) with a susceptible spinach plant and developing a segregating population (e.g. F2 or backcross population) from that cross. The segregating population can then be phenotyped for Pfs resistance and genotyped using e.g. molecular markers such as SNPs (Single Nucleotide Polymorphisms), AFLPs (Amplified Fragment Length Polymorphisms; see, e.g., EP 534 858), or others, and by software analysis molecular markers which co-segregate with the Pfs resistance trait in the segregating population can be identified and their order and genetic distance (centimorgan distance, cM) to the RPF11 resistance gene or locus can be identified. Molecular markers which are closely linked to RPF11 resistance locus, e.g. markers at a 5 cM distance or less, can then be used in detecting and/or selecting plants (e.g. plants of the invention or progeny of a plant of the invention) or plant parts comprising or retaining the introgression fragment comprising the RPF11 resistance gene or locus. Such closely linked molecular markers can replace phenotypic selection (or be used in addition to phenotypic selection) in breeding programs, i.e. in Marker Assisted Selection (MAS). Preferably flanking markers are used in MAS, i.e. one marker on either side of the RPF11 gene or locus.

Any other type of molecular marker and/or other assay that is able to identify the relative presence or absence of a trait of interest (i.e. the RPF11 gene or locus) in a plant or plant part can also be useful for breeding purposes.

Deposit Information

A total of 2500 seeds of spinach NCIMB 42158 were deposited by Nunhems B.V. on 10 Sep. 2013, at the NCIMB Ltd., Ferguson Building, Craibstone Estate, Bucksburn, Aberdeen AB21 9YA, United Kingdom (NCIMB). Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in plant breeding, chemistry, biology, plant pathology or related fields are intended to be within the scope of the following claims.

The present invention will be further illustrated in the following Examples which are given for illustration purposes only and are not intended to limit the invention in any way.

EXAMPLES

Example 1

Pfs Resistance Phenotype of Spinach Comprising the RPF11 Gene

The resistance to downy mildew infection was assayed with the help of a differential set obtained from the Naktuinbouw.

Spinach plants of the invention (comprising the RPF11 gene) were planted along with spinach plants from different other genotypes (see Table 1) in trays containing BVB substrate (Euroveen, Grubbenvorst), and covered with Agravermiculite (Pull, Rhenen). Per test at least 10 plants from one genotype where tested in one or two replications. The trays were placed in a climate cell at 12° C./15° C. (day/night) with a 12 h photoperiod. Plants were inoculated by spraying a sporangial suspension ($2.5 \times 10^5$/ml) of a pathogenic race of *Peronospora farinosa* f. sp. *spinaciae* 14 days after seeding. In this manner pathogenic races were assayed (as shown in Table 2).

The inoculated plants were covered with transparent plastic material with 100% relative humidity for a 24 h period, after this period the plastic was removed on top to lower the relative humidity to 80%.

After 10 days, the plants were scored as 'resistant' or 'susceptible' based on symptoms of pathogen sporulation on the cotyledons and true leaves, as described by Irish et al. (2007; Plant Dis. 91: 1392-1396). Plants exhibiting any evidence of sporulation were considered 'susceptible'. Plants not exhibiting sporulation were considered 'resistant'. Resistant plants were re-inoculated to assess whether plants initially scored as resistant had escaped infection, or whether they were truly resistant. These plants were scored again 10 days after the second inoculation.

Any genotype with <15% of plants being categorized as 'susceptible' (i.e. with >85% of plants categorized as resistant) were considered as a resistant genotype.

Normally the resistance of a spinach hybrid is the effect of two genes, as described by Handke et al. (2000; Gartenbauwissenschaft. 65: 73-78). For example in the hybrid *Andromeda*, the RPF2 resistance gene (Lazio type, resistance against Pfs races) is combined with a RPF3 (Califlay type, resistance against Pfs races 1, 3, 5, 8, 9, 11, 12, and 14) resistance gene. This combination of genes results in resistance to Pfs races 1-12, and 14 and susceptibility to Pfs race 13 (see Table 2). The new resistance gene, RPF11, gave resistance to all tested races. The resistance works both homozygous in fixed lines as in heterozygous backgrounds, like spinach hybrids (see Table 3).

The RPF11 resistance trait of the present invention is conferred by a single dominant resistance gene, which has the great advantage that the RPF11 resistance trait can be easily transferred into other spinach lines or varieties by crossing/introgression, and that it can easily be combined with other resistance genes. The RPF11 gene confers resistance to the tested Pfs races, especially races Pfs 7-14, without the need to use a complimentary resistance gene.

TABLE 2

| Variety | Pfs7 | Pfs8 | Pfs9 | Pfs10 | Pfs11 | Pfs12 | Pfs13 | Pfs14 | UA4712 |
|---|---|---|---|---|---|---|---|---|---|
| Viroflay | + | + | + | + | + | + | + | + | + |
| Resistoflay | + | + | + | + | + | + | + | + | + |
| Califlay | + | − | − | + | − | − | + | − | + |
| Clermont | + | + | + | + | + | + | + | + | − |
| Campania | − | + | + | + | − | + | +/− | + | − |
| Boeing (=Avenger in USA) | − | + | − | + | − | + | − | + | − |
| Lion | − | − | − | + | − | − | − | − | − |
| Lazio | − | − | − | − | + | + | + | + | − |
| Whale | (−) | − | − | + | − | − | + | (−) | + |
| Polka | + | − | − | + | − | − | + | − | + |

TABLE 2-continued

| Variety | Pfs7 | Pfs8 | Pfs9 | Pfs10 | Pfs11 | Pfs12 | Pfs13 | Pfs14 | UA4712 |
|---|---|---|---|---|---|---|---|---|---|
| Pigeon | − | − | − | − | − | − | − | + | + |
| R6 (data from WO2013/064436*) | + | + | − | + | − | − | − | − | |
| Andromeda F1 (US2012/0222147) | − | − | − | − | − | − | + | − | − |
| Parent 1 of Andromeda | + | − | − | + | − | − | + | − | + |
| Parent 2 of Andromeda | − | − | − | − | + | + | + | + | − |
| NCIMB 42158 (RPF11) | − | − | − | − | − | − | − | − | − |

Table 2 shows the differential set of spinach downy mildew races and the resistance of various spinach varieties (hybrids) to each one of these pathogenic races. A susceptible reaction (indicated as "+" in the table) is scored when a successful infection by the fungus is visible as sporulation on the cotyledon or leaf. Resistance (indicated as "−" in the table) is the absence of sporulation on the cotyledons and mature leaves. "(−)" indicates reduced level of infection, often referred to as field resistance=sparse sporulation on the tips of cotyledons. "+/−" indicates variability in the number of resistant and susceptible plants observed. *In WO2013/064436 the R6 gene is described as conferring resistance against Pfs1-6, Pfs9, Pfs11, Pfs12, Pfs13 and Pfs14 (UA4410).

Example 2

Introduction of the RPF11 Resistance Trait into Other Spinach Plants

A plant of the invention was crossed (as a father) with a plant that does not contain the RPF11 resistance gene, to obtain an F1. Thirty plants of the F1 population were tested for resistance to Pfs races 11, 12, 13, and 14 described in Example 1. This particular resistance was absent from the mother plant used in the said cross. All 40 plants showed the resistance pattern of the invention, i.e. resistance to Pfs races 11, 12, 13, and 14. This demonstrated that the RPF11 resistance gene inherits in a dominant manner.

In another experiment, a plant of the invention was crossed (as a mother) with a different spinach plant susceptible to all known races. Plants of the F1 population were selfed, and a total of 1115 plants of the F2 generation were tested for Pfs resistance, as described in Example 1.

It was observed that resistance against Pfs races 2, 5, 10, 11, 12, 13, 14, and UA4712 segregated in the F2 generation in a fashion that corresponds to dominant monogenic inheritance: 835 of the 1115 F2 plants exhibited the RPF11-resistance phenotype. Table 3 gives a detailed overview of the segregation of the RPF11 resistance gene in eight Pfs assays. Chi-square tests confirmed that the observed segregation in the F2 populations was consistent with a 3:1 (resistant:susceptible) segregation of the RPF11 resistance profile.

TABLE 3

| Outcome/Race | Pfs2 | Pfs5 | Pfs10 | Pfs11 | Pfs12 | Pfs13 | Pfs14 | UA4712 | Total |
|---|---|---|---|---|---|---|---|---|---|
| Resistant | 86 (80%) | 87 (76%) | 162 (76%) | 68 (65%) | 81 (76%) | 159 (74%) | 87 (80) | 105 (71%) | 835 (75%) |
| Susceptible | 22 (20%) | 27 (24%) | 50 (24%) | 36 (35%) | 25 (24%) | 55 (26%) | 22 (20%) | 43 (29%) | 280 (25%) |
| Total observations | 108 | 114 | 212 | 104 | 106 | 214 | 109 | 148 | 1115 |
| Chi square probablity | 0.267 | 0.746 | 0.634 | 0.0235 | 0.737 | 0.813 | 0.245 | 0.255 | 0.931 |
| Fitting the expected segregation pattern (p > 0.05) | yes | yes | yes | yes | yes | yes | yes | yes | yes |

Table 3: Overview of segregation of the RPF11 resistance profile in eight Pfs assays, expressed in the number and percentage of plants observed as resistant or susceptible per Pfs race. The plant belong to the progeny of an inbred from a cross between a spinach plant which lacks the RPF11 gene and a genotype of the invention containing the RPF11 gene. Chi-square tests confirm that the results fit the expected segregation pattern for a dominant monogenic trait. In all cases chi-square values are well above 0.05.

Similar segregation results were obtained when the progeny of a cross between a plant that carries the RPF11 resistance gene and a plant not carrying the said gene were assayed for other Pfs races.

The invention claimed is:

1. A cultivated spinach plant comprising resistance against *Peronospora farinosa* races 7-14, wherein said resistance is conferred by a single, dominant resistance gene, which is the resistance gene present in seeds deposited under accession number NCIMB 42158.

2. The plant according to claim 1, wherein the spinach plant further comprises resistance against *Peronospora farinosa* races 1, 2, 5 and 6.

3. The plant according to claim 1, wherein the spinach plant further comprises resistance against isolate UA4712.

4. The plant according to claim 1, wherein said spinach plant is a hybrid plant.

5. The plant according to claim 1, wherein said spinach plant is an inbred plant.

6. The plant according to claim 1, wherein the spinach plant is savoy, semi-savoy, flat- or smooth leaved.

7. A seed from which a plant according to claim 1 can be grown.

8. A leaf of a plant according to claim 1.

9. A progeny plant of a spinach plant according to claim 1, wherein said progeny plant retains the resistance gene which confers resistance to *Peronospora farinosa* races 7-14.

10. The progeny plant according to claim 9, wherein said progeny plant is resistant to *Peronospora farinosa* races 1-14 and isolate UA4712.

11. The progeny plant according to claim 9, wherein the progeny plant is produced by one or more methods of selfing, crossing, mutation, double haploid production or transformation.

12. A method of generating a spinach plant comprising resistance against *Peronospora farinosa* races 7-14, wherein said resistance is conferred by a single, dominant resistance gene, comprising growing a plant from a seed deposited under accession number NCIMB 42158 or a progeny thereof, wherein said progeny comprises the single, dominant resistance gene which confers resistance to *Peronospora farinosa* races 7-14 gene, which is the resistance gene present in seeds deposited under accession number NCIMB 42158.

13. The method of claim 12 wherein the single, dominant resistance gene further confers resistance against *Peronospora farinosa* races 1, 2, 5 and 6.

14. A part of the spinach plant according to claim 1, wherein the part is a stem, a cutting, a petiole, a cotyledon, a flower, an anther, a pollen, an ovary, a root, a root tip, a protoplast, a callus, a microspore, a stalk, an ovule, a shoot, a seed, an embryo, an embryo sac, a cell, a meristem, a bud or a leaf.

15. A cell culture or tissue culture comprising a cell or a tissue derived from a part of a spinach plant comprising resistance against *Peronospora farinosa* races 7-14, wherein said resistance is conferred by a single, dominant resistance gene, which is the resistance gene present in seeds deposited under accession number NCIMB 42158.

16. A spinach plant regenerated from the cell culture or tissue culture of claim 15 and comprising resistance against *Peronospora farinosa* races 7-14, wherein said resistance is conferred by a single, dominant resistance gene, which is the resistance gene present in seeds deposited under accession number NCIMB 42158.

17. A method for generating a spinach plant comprising resistance against *Peronospora farinosa* races 7-14 comprising:
  a) crossing a spinach plant comprising an introgression fragment present in seeds deposited under accession number NCIMB 42158, wherein said introgression fragment confers resistance against *Peronospora farinosa* races 7-14, which is the resistance gene present in seeds deposited under accession number NCIMB 42158, with another spinach plant, which is susceptible to one or more of *Peronospora farinosa* races 7-14 to produce F1 seeds;
  b) selfing a plant grown from the F1 seeds one or more times to produce F2, F3 or further generation selfing progeny; and
  c) identifying spinach plants grown from F1, F2, F3 or further generation selfing progeny which have resistance against *Peronospora farinosa* races 7-14, wherein said resistance is conferred by a single, dominant resistance gene, which is the resistance gene present in seeds deposited under accession number NCIMB 42158.

18. A spinach plant obtained by the method of claim 17, said spinach plant comprising resistance against *Peronospora farinosa* races 7-14, wherein said resistance is conferred by a single, dominant resistance gene, which is the resistance gene present in seeds deposited under accession number NCIMB 42158.

19. The seed of claim 7, wherein a representative sample of the seed has been deposited under accession number NCIMB 42158.

20. The method of claim 17, further comprising
  d) crossing said identified F1, F2, F3 or further generation selfing progeny of step c) to the susceptible spinach plant of step a), to produce a backcross progeny; and
  e) selecting a backcross progeny which comprises resistance against *Peronospora farinosa* races 7-14, wherein said resistance is conferred by a single, dominant resistance gene, which is the resistance gene present in seeds deposited under accession number NCIMB 42158.

21. A method for generating a spinach plant comprising resistance against *Peronospora farinosa* races 7-14 comprising:
  a) crossing a spinach plant comprising resistance against *Peronospora farinosa* races 7-14, wherein said resistance is conferred by a single, dominant resistance gene, which is the resistance gene present in seeds deposited under accession number NCIMB 42158 with another spinach plant, which is susceptible to one or more of *Peronospora farinosa* races 7-14 to produce F1 seeds; and
  b) growing said F1 seeds.

* * * * *